Figure 1:
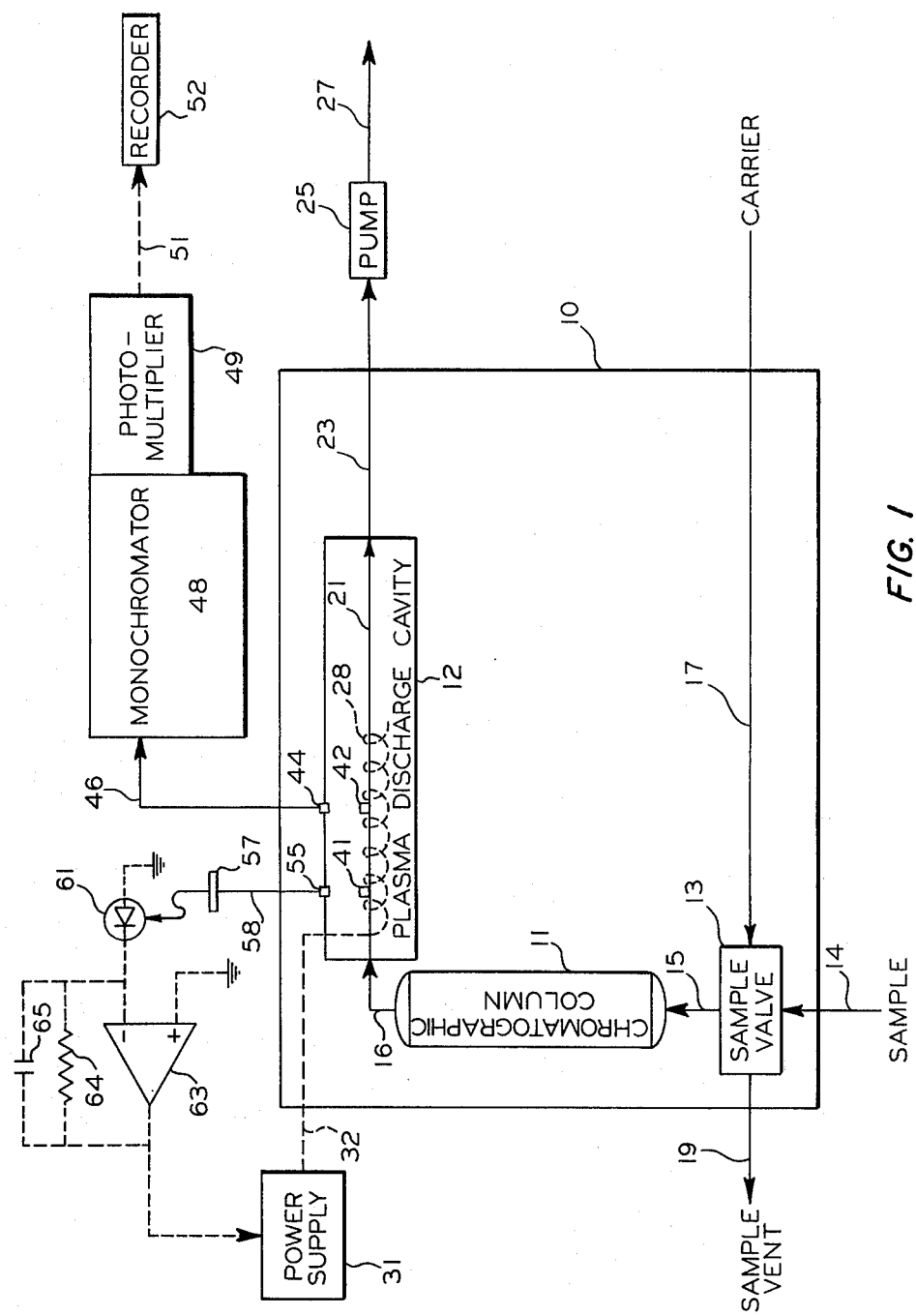

United States Patent [19]

Walker

[11] 4,256,404
[45] Mar. 17, 1981

[54] OPTOELECTRONIC FEEDBACK CONTROL FOR A SPECTROMETER

[75] Inventor: Starnes E. Walker, Bartlesville, Okla.

[73] Assignee: Phillips Petroleum Company, Bartlesville, Okla.

[21] Appl. No.: 79,747

[22] Filed: Sep. 28, 1979

[51] Int. Cl.³ .......................................... G01N 21/68
[52] U.S. Cl. .................................... 356/316; 250/205; 315/151; 315/158
[58] Field of Search ............... 356/316, 313; 313/231, 313/231.3, 231.4, 231.5, 231.6; 315/111.2, 149, 151, 158; 250/205

[56] References Cited

U.S. PATENT DOCUMENTS

| | | | |
|---|---|---|---|
| 2,745,311 | 5/1956 | Touvet | 356/316 X |
| 3,215,843 | 11/1965 | Neil | 315/151 X |
| 3,278,796 | 10/1966 | Takei et al. | 313/231.6 X |
| 3,297,860 | 1/1967 | Weiss | 356/316 X |
| 3,396,303 | 8/1968 | Gordon | 315/158 X |
| 3,467,471 | 9/1969 | Greenfield et al. | 356/316 X |
| 3,484,650 | 12/1969 | Rendina | 356/316 X |
| 3,610,759 | 10/1971 | Wood, Jr. | 356/316 |
| 3,645,629 | 2/1972 | Dagnall | 356/316 X |
| 3,786,308 | 1/1974 | Browner et al. | 356/316 X |
| 3,958,883 | 5/1976 | Turner | 356/316 |
| 3,996,494 | 12/1976 | Suga | 315/158 X |

OTHER PUBLICATIONS

Durrant et al., *Laboratory Equipment Digest*, vol. 11, No. 4, Apr. 1973, pp. 156-160.
Censidine, *Encyclopedia of Instrumentation and Control*, McGraw-Hill Book Co., pp. 276-280, 1971.

*Primary Examiner*—F. L. Evans

[57] ABSTRACT

Long-term stability for an emission type plasma spectrometer is provided by automatically adjusting the output of a power supply which is being utilized to create the plasma. The automatic adjustment is based on a feedback signal which is derived by monitoring an atomic line of a carrier gas.

8 Claims, 1 Drawing Figure

OPTOELECTRONIC FEEDBACK CONTROL FOR A SPECTROMETER

This invention relates to plasma spectroscopy. In one aspect this invention relates to method and apparatus for stabilizing an emission type plasma spectrometer.

Emission type plasma spectrometers are well known in the analysis art. In an emission type plasma spectrometer, a sample gas is converted into a highly ionized and dense plasma in which the molecules are disassociated into their respective atoms. A radio frequency (RF) power supply may be utilized to create the plasma. Energy is emitted at certain wave lengths depending upon the elements present. The wave lengths at which the energy is emitted are generally referred to as atomic emission lines. The atomic emission lines may be monitored to provide an indication of the concentration of the atoms present in the plasma.

While it is well known that an emission type plasma spectrometer is a powerful analysis tool, it is also well known that emission type plasma spectrometers are extremely susceptible to external perturbations of temperature, vibration, optical coupling and the like. Optical coupling can be an especially significant problem because clouding of the lenses being utilized to monitor the atomic emission lines is extremely common in emission type plasma spectrometers and this clouding results in a lower monitored emission level over a period of time even though the concentration of the atoms may be remaining constant over the same period of time. Because of the instability of emission type plasma spectrometers, the technique has generally not been applied for continuous analysis of processes even though the emission type plasma spectrometers provide higher sensitivity than the more commonly used absorption type instruments for certain analysis.

It is thus an object of this invention to provide method and apparatus for a stabilizing an emission type plasma spectrometer in such a manner that an emission type plasma spectrometer may be applied to continuous analysis of processes over a substantial period of time.

In accordance with the present invention, method and apparatus is provided whereby an atomic emission line associated with the carrier gas which is being utilized to carry the sample gas through the emission type plasma spectrometer is monitored. Preferably, the wavelength of the monitored atomic emission line associated with the carrier gas is not close to the wavelength of any atomic emission line associated with the sample gas. Since the flow rate of the carrier gas is maintained substantially constant, the intensity of the atomic emission line associated with the carrier gas should remain substantially constant. The intensity of the atomic emission line associated with the carrier gas is utilized to derive a feedback signal which is utilized to automatically manipulate the output from a power supply which is being utilized to create the plasma. If the intensity of the atomic emission line associated with the carrier gas should change, the power output from the power supply is changed to compensate for whatever factor is contributing to the decrease in the intensity of the atomic emission line associated with the carrier gas. In this manner, long-term stability of the emission type plasma spectrometer is provided and the emission type plasma spectrometer may be utilized as an analysis instrument over a substantial period of time without recalibration.

Other objects and advantages of the invention will be apparent from the foregoing brief description of the invention and the claims as well as from the detailed description of the drawing in which:

FIG. 1 is a diagrammatic illustration of an emission type plasma spectrometer together with the optoelectronic feedback control of the present invention.

The invention is described in terms of an emission type plasma spectrometer which is associated with a chromatographic column and a chromatographic analyzer sample valve. However, the invention is not limited to use with a chromatographic column and a chromatographic analyzer sample valve. The gas to be analyzed may be provided directly to the emission type plasma spectrometer if analysis of the total concentration of a particular element is desired.

The invention is described in terms of an emission type plasma spectrometer in which an RF power supply is utilized to create the plasma and in which particular equipment is utilized to monitor particular atomic emission lines. The invention is however applicable to other techniques for creating a plasma and is also applicable to other procedures for monitoring atomic emission lines.

The invention is also described in terms of particular electronic circuitry for generating the optoelectronic feedback control signal. However, the invention is applicable to any method and apparatus for generating a feedback control signal based on an atomic emission line associated with the carrier fluid flowing through the emission type plasma spectrometer.

Referring now to the drawing, there is illustrated a chromatographic column 11, a plasma discharge cavity 12 and a sample valve 13 all of which are located inside the chromatographic oven 10. A sample of a fluid to be analyzed is delivered to sample valve 13 through conduit means 14. A conduit means 15 extends between the sample valve 13 and the inlet to the chromatographic column 11. A conduit means 16 extends between the outlet of chromatographic column 11 and the inlet of the plasma discharge cavity 12. Carrier fluid is provided to the sample valve 13 through conduit means 17. The sample is vented from the sample valve 13 through conduit means 19.

At the beginning of an analysis period, sample valve 13 is actuated to introduce a predetermined volume of sample into the carrier fluid flowing through the chromatographic column 11. The constituents of the sample are eluted in sequence and flow from the chromatographic column 11 through conduit means 16 to the plasma discharge cavity 12.

Conduit means 14, 17, 15, 19 and 16 are preferably formed from stainless steel. Conduit means 21 which extends through the plasma discharge cavity 12 is preferably formed from quartz tubing. The effluent flowing through conduit means 16 flows through the quartz tubing 21 and then flows through conduit means 23, which is preferably stainless steel, to the pump 25. The effluent flowing through conduit means 23 is vented through conduit means 27.

A coil 28 extends for at least a portion of the length of the conduit means 21. Power is supplied to the coil 28 from the power supply 31 through the electrical conductor 32. The plasma discharge cavity 12 is preferably formed from metal in such a manner that the plasma discharge cavity 12 forms an infinite ground plane. The size of the coil 28 and the physical dimensions of the plasma discharge cavity 12 are selected in such a manner that an electric field is focused along the quartz conduit 21. The manner in which this is accomplished is well known in the art of emission type plasma spectrometers. Generally, the higher the frequency of the voltage supplied from the power supply 31 the smaller the size of the coil 28 and the plasma discharge cavity 12.

The effluent flowing from conduit means 21 is converted into a highly ionized and dense plasma in which the molecules are disassociated into the respective atoms. This results in the emission of energy at particular wave lengths depending upon the elements present in the effluent flowing through conduit means 21. Two optical windows 41 and 42 are provided in the quartz tubing 21 to enable the monitoring of the atomic emission lines associated with the effluent flowing through conduit means 21.

An optical window 44 is provided in the plasma discharge cavity 12. The optical window 44 is located substantially opposite the optical window 42. Emissions from the effluent flowing through conduit means 21 are provided through the optical window 42 and the optical window 44 and are transmitted through the quartz fiber optic wave guide 46 to the monochromator 48. The monochromator 48 acts as a filter to select one of the wave lengths to be monitored. The photo multiplier 49 amplifies the energy associated with that particular wave length and provides a DC signal 51 to the recorder 52. The voltage level of the DC signal 51 may be utilized to determine the concentration of particular elements in the effluent flowing through conduit means 21. The manner in which the monochromator 48 and the photo multiplier 49 operate is well known in the art and these devices are commercially available.

A second window 55 is provided in the plasma discharge cavity 12. The second optical window 55 is located substantially opposite the optical window 41. Emissions from the effluent flowing through conduit means 21 are provided through the optical window 41 and the optical window 55 and are transmitted to the optical interference filter 57 through the quartz fiber optic wave guide 58. The interference filter 47 filters all of the wave lengths except a particular wave length of an atomic emission line for the carrier fluid flowing through conduit means 17. Energy associated with this wave length is provided through the interference filter 57 and impinges upon the photodiode 61. The anode of the photodiode 61 is tied to ground. The cathode of the photodiode 61 is tied to the inverting input of the operational amplifier 63. The noninverting input of the operational amplifier 63 is tied to ground. The output of the operational amplifier 63 is tied to the power supply 31 and is also fed back through the combination of the resistor 64 and capacitor 65 to the inverting input of the operational amplifier 63. The operational amplifier 63 together with the resistor 64 and the capacitor 65 comprises a conventional current to voltage conversion circuit. The output signal from the operational amplifier 63 is utilized to automatically vary the output from the power supply 31 as required to maintain the energy impinging upon the photodiode 61 substantially constant. This is accomplished by subtracting the feedback signal from the output of the power adjustment knob of the power supply 31. This allows the feedback signal to adjust the output power in the same manner as an operator adjusting the front panel knob.

Temperature variations to which the plasma discharge cavity 12 is subjected are substantially reduced by placing the plasma discharge cavity 12 as well as the chromatographic column 11 and the sample valve 13 inside the chromatographic oven 10. The primary factor which affects the stability of the emission type plasma spectrometer illustrated in FIG. 1 is deposits of materials on the quartz tubing 21 and thus on the windows 41 and 42. These deposits affect the stability of the emission type plasma spectrometer by reducing the emissions produced by a constant concentration of a particular element. To compensate for this, the present invention provides the optoelectronic feedback which is based on the energy emitted at a certain wave length associated with an atomic emission line for the carrier fluid flowing through conduit means 17. The flow of the carrier fluid flowing through conduit means 17 is maintained substantially constant. Thus the energy emitted at the wave length of an atomic emission line for the carrier fluid should be substantially constant. As deposits are formed on the optical window 41, the energy impinging on the photodiode 61 will be decreased. The optoelectronic feedback causes the power output from the power supply 31 to be increased until the energy impinging upon the photodiode 61 returns to the level for which the emission type plasma spectrometer was calibrated. This process is continued until it becomes undesirable to further increase the power output from the power supply 31. At this point, the quartz tube 21 is removed and is either cleaned or replaced. The emission type plasma spectrometer is recalibrated and the process is then continued. The use of the optoelectronic feedback provides long-term stability of the emission type plasma spectrometer which enables the emission type plasma spectrometer to be utilized as an analysis instrument in a continuous process.

The invention has been described in terms of a preferred embodiment as is illustrated in FIG. 1. The chromatographic oven 10, the chromatographic column 11 and the sample valve 13 are each available with the Model 102 Gas Chromatograph manufactured by Applied Automation Inc., Bartlesville, Oklahoma. The monochromator 48 and the photo multiplier 49 are commercially available. The Model EV-700 Monochromator manufactured by GCA-McPherson, Acton, MA, may be utilized if desired. In like manner, the power supply 31 is commercially available. The Model 350L manufactured by ENI, Rochester, NY, may be utilized if desired. This power supply provides possibly 10 watts of power at a frequency of 27 megahertz which is presently preferred. The optical windows, fiber optic wave guides and interference filters utilized are also commercially available from a number of manufacturers as is the electrical components associated with the feedback circuit. Preferably, the capacitor 65 has a capacitance on the order of 5,000 picofarads while the resistor 64 has a value of approximately 1,000 megohms. This gives a time constant of approximately 5 seconds for the integration circuit. The plasma discharge cavity 12 is preferably machined from copper. The cavity is preferably 4 inches long with an outside diameter of 2 inches and an inside diameter of one inch.

While the invention has been described in terms of the presently preferred embodiment, reasonable variations and modifications are possible by those skilled in the art, within the scope of the described invention and the appended claims.

That which is claimed is:

1. Apparatus comprising:
    means defining a plasma discharge cavity;

means for providing a carrier gas and a sample gas to said plasma discharge cavity;

means for converting at least a portion of said carrier gas and said sample gas into a plasma inside said plasma discharge cavity;

means for detecting the energy associated with an atomic emission line of said carrier gas;

means for establishing a feedback control signal which is responsive to the level of the detected energy associated with said atomic emission line of said carrier gas;

means for manipulating said means for converting at least a portion of said carrier gas and said sample gas into a plasma in response to said feedback control signal to thereby maintain the level of the detected energy associated with said atomic emission line of said carrier gas substantially constant;

means for detecting the energy associated with an atomic emission line of said sample gas; and means for establishing an output signal which is representive of the concentration of a particular element in said sample gas in response to the level of the detected energy associated with said atomic emission line of said sample gas.

2. Apparatus in accordance with claim 1 wherein said means for providing a carrier gas and a sample gas to said plasma discharge cavity comprises:

a chromatographic separation column means;

means for passing a stream of said carrier gas to said chromatographic separation column means;

means for injecting said sample gas into the stream of said carrier gas flowing to said chromatographic separation column means;

a quartz tube extending through said plasma discharge cavity; and means for passing the stream of said carrier gas containing separated components of said sample gas from said chromatographic separation column means through said quartz tube and thus through said plasma discharge cavity.

3. Apparatus in accordance with claim 2 wherein said means for converting at least a portion of said carrier gas and said sample gas into a plasma inside said plasma discharge cavity comprises:

a coil surrounding said quartz tube and extending for at least a portion of the length of said quartz tube;

a radio frequency power supply means; and means for supplying a voltage having a desired frequency from said radio frequency power supply means to said coil to thereby create an electric field which is directed along said quartz tube.

4. Apparatus in accordance with claim 3 wherein said means for detecting the energy associated with an atomic emission line of said carrier gas comprises:

a first optical window operably located in said quartz tube;

a second optical window located substantially opposite said first optical window in said plasma discharge cavity;

an interference filter;

a fiber optic wave guide extending between said second optical window and said interference filter; and a photodiode, the emissions from said plasma being transmitted through said first optical window, said second optical window, said fiber optic wave guide and said interference filter to said photodiode, said interference filter filtering substantially all wave lengths of the energy transmitted through said fiber optic wave guide except the wave length of an atomic emission line associated with said carrier gas.

5. Apparatus in accordance with claim 4 wherein said means for establishing said feedback control signal which is responsive to the level of the detected energy associated with said atomic emission line of said carrier gas comprises:

an operational amplifier having an inverting input, a noninverting input and an output;

means for connecting the anode of said photodiode to the inverting input of said operational amplifier;

means for grounding the noninverting input of said operational amplifier;

a resistor means;

a capacitor means;

means for feeding the output of said operational amplifier back to the inverting input of said operational amplifier through the parallel combination of said resistor means and said capacitor means, said feedback control signal being established as the output of said operational amplifier.

6. Apparatus in accordance with claim 5 wherein said means for manipulating said means for converting at least a portion of said carrier gas and said sample gas into a plasma in response to said feedback control signal comprises:

means for supplying the output from said operational amplifier to said radio frequency power supply means; and means for manipulating the output of said radio frequency power supply means in response to the voltage level of the output from said operational amplifier.

7. A method for stabilizing an emission type plasma spectrometer comprising the steps of:

passing a carrier gas and a sample gas to said emission type plasma spectrometer;

detecting the energy associated with an atomic emission line of said carrier gas;

establishing a feedback control signal which is responsive to the level of the detected energy associated with said atomic emission line of said carrier gas;

manipulating the energy supplied to said emission type plasma spectrometer in response to said feedback control signal to thereby maintain the level of the detected energy associated with said atomic emission line of said carrier gas substantially constant;

detecting the energy associated with an atomic emission line of said sample gas; and establishing an output signal which is representive of the concentration of a particular element in said sample gas in response to the level of the detected energy associated with said atomic emission line of said sample gas.

8. A method in accordance with claim 7 wherein said step of establishing said feedback control signal comprises:

converting said detected energy to an electrical signal; and integrating said electrical signal to thereby establish said feedback control signal.

* * * * *